United States Patent [19]

Cassou

[11] Patent Number: 5,006,117
[45] Date of Patent: Apr. 9, 1991

[54] CONTAINER FOR BIOLOGICAL LIQUIDS

[75] Inventor: Robert Cassou, L'Aigle, France

[73] Assignee: Instruments Medecine Veterinaire, L'Aigle, France

[21] Appl. No.: 297,433

[22] Filed: Jan. 17, 1989

[51] Int. Cl.$^5$ .............................................. A61B 19/00
[52] U.S. Cl. ..................................... 604/403; 600/33; 600/34
[58] Field of Search ............... 604/403, 408, 411, 415, 604/416; 600/33–35; 215/1 C, 247, 248, 250; 220/DIG. 34

[56] References Cited

U.S. PATENT DOCUMENTS

| 2,698,619 | 1/1955 | Beacham et al. | 604/415 X |
| 2,704,075 | 3/1955 | Cherkin | 604/408 |
| 3,424,218 | 1/1969 | Vanderbur et al. | 150/5 |
| 3,474,789 | 10/1969 | Soto | 128/272 |
| 4,326,574 | 4/1982 | Pallaroni et al. | 604/415 |
| 4,528,220 | 7/1985 | Hwo | 428/35 |
| 4,534,467 | 8/1985 | Rathbun | 206/350 |
| 4,576,602 | 3/1986 | Levin et al. | 604/408 |
| 4,700,838 | 10/1987 | Falciani et al. | 206/438 |
| 4,902,286 | 2/1990 | Ranoux | 604/403 |

FOREIGN PATENT DOCUMENTS 0180543  5/1986  European Pat. Off.
8702879  5/1987  PCT Int'l Appl.

Primary Examiner—Robert A. Hafer
Assistant Examiner—Kevin G. Rooney
Attorney, Agent, or Firm—Young & Thompson

[57] ABSTRACT

A container for biological liquids such as a culture medium comprises a hollow body of elastomeric material including a tubular intermediate part, rounded ends and a portion perforable by a cannula for introducing the biological liquid and hermetically resealing itself once the cannula is removed. The interior and exterior surfaces of the hollow body are smooth and curved throughout and the portion perforable by the cannula is thick walled and is preferably provided at one or both ends of the hollow body. The container may comprise two half shells joined together or a blow extruded member. The interior surface is advantageously coated to eliminate asperities.

12 Claims, 2 Drawing Sheets

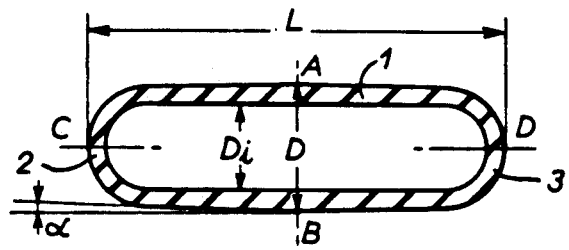
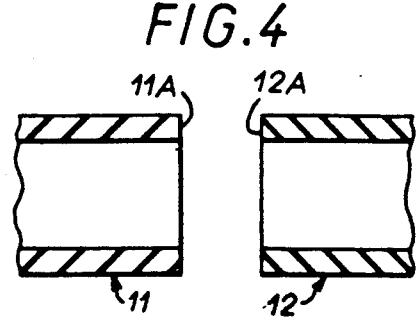
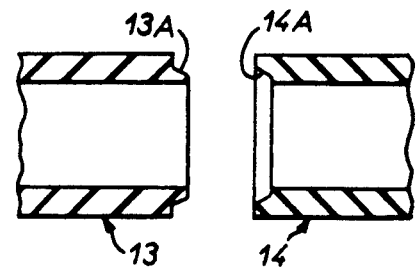
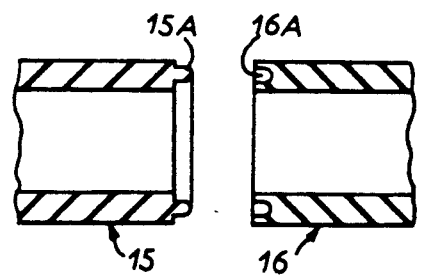
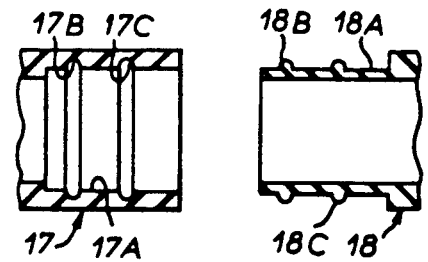
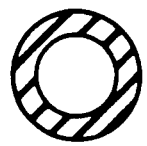
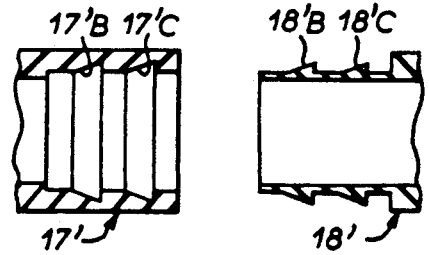

CONTAINER FOR BIOLOGICAL LIQUIDS

BACKGROUND OF THE INVENTION

The present invention relates to a container for biological liquids and more particularly culture media.

The need for such a container has arisen particularly for the fertilization of ovocytes according to the technique described in International publication WO 87/02879 published May 21, 1987.

Such a container must satisfy a number of desiderata: (1) confinement of a culture medium under perfectly sterile conditions, free of contact with air; (2) devoid of asperities on the exterior surface in order to avoid the risk of trauma in case of implantation in a body cavity such as the vagina; and (3) an interior surface which is as smooth as possible on account of any cavity or surface roughness seriously jeopardizing the development of embryos and their subsequent transfer.

Prior art containers are far from satisfactory; they have too complicated a structure and are difficult to employ in the intended conditions of use.

Vanderburg, Jr. U.S. Pat. No. 3,424,218 discloses in particular a container for liquids intended for infusion and comprises a hollow body of plastic material having closure member with a reduced central portion for insertion of a cannula for dispensing the liquid and almost completely resealing thus renewing hermeticity after removal of the cannula. However, the container disclosed has a closure member which has sharp edges on both its exterior and interior surfaces. Moreover the reduced central portion for the insertion of the cannula is defined by a thin membrane which is thinner than the wall thickness of the rest of the container which is liable to jeopardize hermetic resealing after puncture and withdrawal of the cannula.

OBJECT AND SUMMARY OF THE INVENTION

An object of the present invention is to provide a container of simple structure which is capable of satisfying all the desiderata indicated above.

According to the invention there is provided a container for a biological liquid such as a culture medium, comprising a hollow body of plastic material including means perforable by a canulla for introducing a biological fluid and hermetically resealing itself upon withdrawal of the cannula. The improvement comprises the interior and exterior surfaces of the container being smooth and curved throughout and the means perforable by a cannula comprising a thick wall portion.

Such a container enables the introduction of one or more liquids by means of a cannula, the elasticity permits the container to resume to its original volume after temporary contraction.

The container which is preferably ovoid lends itself after industrial fabrication to at least partial filling with a culture or conservation medium anaerobically, enabling the subsequent introduction of one or more ovocytes by means of such a cannula as well as sperm in order to effect in vitro and/or in vivo fertilization.

The configuration and fluidtightness of the container enables it to be implanted into a vagina for a predetermined period, for example 48 hours.

After this period has elapsed an end of the container can be cut off and the contents emptied into a Petri dish to examine with a magnifying glass the results of fertilization and to transfer, if appropriate, one or more embryos to the uterus of the woman for insemination.

According to an embodiment of the invention the container comprises an assembly of two molded half shells or container parts.

According to another embodiment the container is fabricated by blow extrusion of an elastomeric material preferably of the type which vulcanizes at ambient temperature.

The interior wall of the container may advantageously be lined with a coating produced by injection and centrifugation of a metered quantity of an elastomeric material vulcanizable at ambient temperature.

These and other features and advantages of the invention will become apparent from the description which follows with references to the accompanying drawings.

BRIEF DESCRIPTION OF THE DRAWINGS

FIG. 1 is a longitudinal sectional view of a first embodiment of the container of ovoid configuration;

FIG. 2 is a similar longitudinal sectional view of another embodiment of the container having a thick end wall portion;

FIG. 2A is a cross section taken on the line X—X of FIG. 2.

FIG. 3 is a similar longitudinal sectional view for a further embodiment having two thick end wall portions;

FIG. 4 is a detail sectional view on an enlarged scale illustrating a first butt joint connection for assembling the container parts;

FIG. 5 is a view similar to that of FIG. 4 for another joint;

FIG. 6 is a view similar to that of FIG. 4 for a tongue and groove joint;

FIG. 7 is a view similar to that of FIG. 4. for a tongue and groove connection provided on the inner and outer walls of the respective container parts; and FIG. 8 is a view similar to that of FIG. 7. for a different kind joint with buttress teeth;

DETAILED DESCRIPTION OF THE PREFERRED EMBODIMENTS OF THE INVENTION

Figure 9:
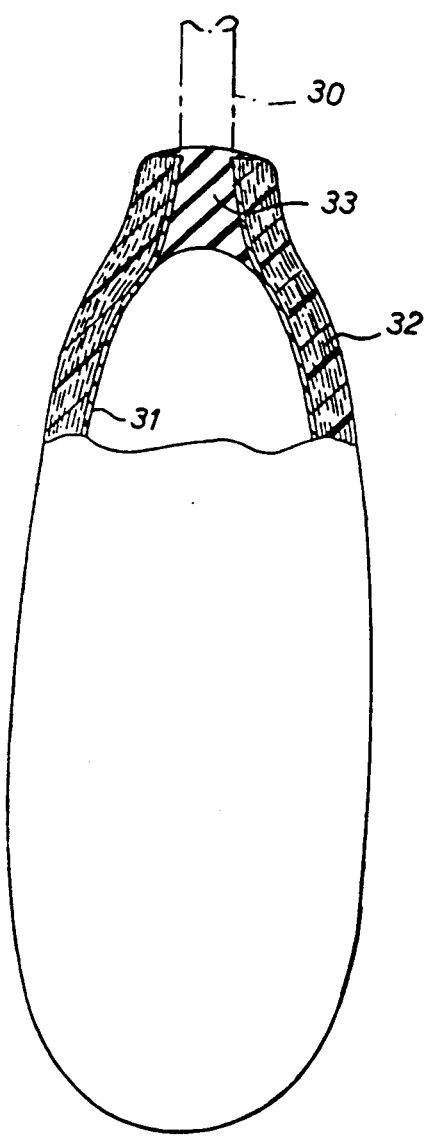
FIG. 9 is an elevational view partly cut away showing a method of fabrication of the container by blow extrusion.

According to the embodiment illustrated in FIG. 1, a container according to the invention comprises a hollow body 1 of generally tubular configuration extending between two substantially hemispherical end walls 2, 3.

The container comprises two half shells or container parts adapted to be assembled together along a transverse connecting plane A-B or a longitudinal connecting plane C-D.

The constituent material is preferably a synthetic elastomer selected from the group comprising butadiene styrene copolymers, nitrile acrylic polymers, polychlorobutadiene and polyisobutylene.

In the illustrated embodiment the total length L of the container is 50 mm, the maximum outer diameter is 15 mm tapering at a slight slope of 1.5° towards the end walls, whereas the inner diameter Di is 10 mm along the tubular hollow body. Thus the wall thickness gradually increases from 2 mm at the end walls to 2.5 mm at the plane A–B.

. Experience has shown that a hollow body thus fabricated of an elastomeric material such as polyisobutylene is adapted to be perforated with a cannula and resealed upon removal of the same.

Under these conditions a biological liquid may be introduced into the container by means of a first cannula intended to vent contained air to the atmosphere and a second cannula for feeding in the biological liquid fluid, such as a culture medium. The introduction of the biological liquid gradually forces out the contained air. Once excess liquid reaches the first cannula, filling is terminated and the anaerobic confinement of the biological liquid is ensured.

The embodiment of FIG. 2 differs from that of the preceding embodiment by the provision of a thick end wall 2A at one end, which end wall is generally frustoconical. In the illustrated embodiment the thick end wall or pad comprises a first portion 21 having a diameter at its base equal to that of the inner diameter Di of the hollow body, here 10 mm, the diameter of the frustum decreasing to 8 mm with a half cone angle of 12°, and a second portion 22 having a diameter decreasing from about that of diameter D2 of about 6 mm to a free end diameter D3 of about 4 mm.

The thick end wall 2A has the advantage of increasing the resealing capacity after removal of the cannula(s).

The embodiment of FIG. 3 differs from the preceding embodiment by the provision of thick end walls 2A and 3A at each of the extremities of the containers.

FIGS. 4–8 show various types of assembly for joining two half shells or container parts along a diametrical plane.

FIG. 4 shows a butt joint connection between respective half shells or container parts 11, 12 having respective free edges 11A, 12A perpendicular to the longitudinal axis. The assembly of the free edges may be effected after bringing them together, for example, by ultrasonic or hot air welding.

FIG. 5 illustrates the assembly of containers parts along their free edges, half shell or container part 13 having a frustoconical projection 13A and the other shell half or container part 14 having a complementary frustoconical recess 14A adapted to mate with the frustoconical projection 13A.

FIG. 6 shows an annular tongue and groove type assembly of the opposed free edges of the respective half shells or container parts 15, 16. The half shell 15 has an annular tongue 15A with a rounded end and the other half shell 16 has a complementary annular groove 16A adapted to mate with the annular tongue 15A.

In the embodiment of FIG. 7 the half shell 17 has a socket end portion 17A having two axially spaced annular grooves 17B, 17C whereas the half shell 18 has a complementary projecting end portion 18A adapted to be fitted inside the socket end portion 17A, annular beads 18B, 18C coming into mating engagement with complementary annular grooves 17B, 17C. The insertion of the projecting end portion 18A into the socket end portion 17A is enabled by elastic deformation of the constituent material. In this embodiment the half shell 17 is made of an elastomer having a Shore hardness of about 44, the half shell 18 having a Shore hardness of about 80. Experience seems to show that satisfactory adherence can be obtained upon assembly thereby making the use of an adhesive or heat welding superfluous.

Finally, the embodiment of FIG. 8 distinguishes from the preceding embodiment only by the fact that the grooves 17'A, 17'B of the socket end portion 17' and the ribs 18'B, 18'C on the projecting end portion 18' are generally of triangular section to define buttress teeth.

The fact that the half shells 18, 18' with the projecting end portions are harder than the half shells 17, 17' having the socket end portions has the advantage of maintaining the tubular configuration with enhanced crush resistance in the connecting zone of the assembled container.

For this reason, in the embodiment of FIG. 2, it is preferred to have the thick end wall or pad 2A on the half shell 17, 17' of lesser Shore hardness.

Instead of molding two half shells and assembling them with one of the preceding joints, the invention also contemplates the application of a method of fabrication by blow extrusion.

Thus in the schematic drawing of FIG. 9 a tube 30 is fabricated by blow extruding an initial hollow body or pre-form 31 of blow extrudable plastic material.

Thereafter the hollow body or pre-form is dipped repeatedly into a latex bath to form a plurality of layers or coatings 32. After stabilizing the resulting multi-layered hollow body the blow tube 30 is severed and the blow hole is closed off with a cold vulcanizable silicone mastic such as sold under the trade mark Rodorsil. The resulting stopper 33 defines a thick wall portion adapted to be perforated by a cannula. The resulting hollow body is of unitary multi-layered construction with a thick wall portion according to a feature of the present invention.

The interior layers 31 are made of a material which is selected to be biocompatible for the specific desired application.

Figure 10:
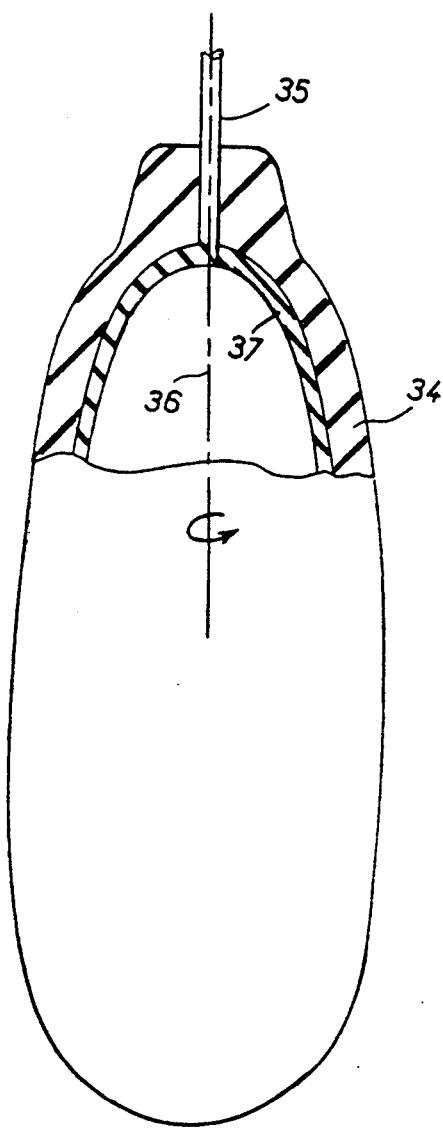
FIG. 10 is an elevational view partly cut away showing an inner lining formed by injection and centrifugation.

It is possible to envisage as shown in FIG. 10 the formation of an interior lining 37 inside a hollow body 34 after its fabrication by introducing through a cannula 35 coaxial with the axis 36 of the hollow body an appropriate metered quantity of a cold vulcanizable elastomer which is spread over the interior surface through centrifugal force by rotating the body 34 about the axis 36. The interior has a flawless surface, devoid of any asperities which are overcoated by the elastomer prior to vulcanization.

This technique for improving the surface condition of the container may be employed on the molded containers according to the embodiments of FIGS. 1–8.

What I claim is:

1. An in-vivo fertilization container for a biological liquid such as a culture medium, comprising a hollow body of plastic material including means perforable by a cannula for introducing a biological liquid and hermetically resealing itself upon withdrawal of the cannula, the hollow body having a generally cylindrical tubular portion between rounded end portions, the interior and exterior surfaces of the container being smooth, continuous and curved throughout and the means perforable by a cannula comprising a thick wall portion, said thick wall portion comprising one of said end portions and being substantially thicker in a direction axially of the container than said cylindrical tubular portion and being integral with said cylindrical tubular portion.

2. A container according to claim 1, wherein the thick wall is of generally outwardly tapering frustoconical configuration with rounded edges.

3. A container according to claim 1, wherein said thick wall portion comprises an elastomeric pad.

4. A container according to claim 1, comprising two half shells assembled by a joint, the interior wall surface of the container remaining continuous.

5. A container according to claim 4, wherein the half shells are made of elastomeric materials having different hardnesses for enhanced crush resistance adjacent a connecting zone between the shells.

6. A container according to claim 1, wherein the inner surface of the container includes a cylindrical wall connected to rounded walls at each end.

7. A container according to claim 1, wherein the interior and exterior walls of the container are ovoid.

8. A container according to claim 7, further comprising a laminated interior lining of biocompatible plastic material and multi-layered coating.

9. A container according to claim 1, wherein the plastic material is an elastomer.

10. A container according to claim 1, wherein said thick wall portion has a location for inserting a cannula for introducing the biological liquid and a location for inserting a cannula for venting container air to the atmosphere.

11. A container according to claim 2, wherein a said thick wall portion is disposed at each of said end portions.

12. A container according to claim 1, wherein the inner diameter of said hollow body is about ⅔ of the outer diameter of the cylindrical tubular portion of the hollow body.

* * * * *